United States Patent [19]
Ambler et al.

[11] Patent Number: 4,838,327
[45] Date of Patent: Jun. 13, 1989

[54] RECEPTACLE BAG ASSEMBLY

[76] Inventors: Kevin Ambler, 16496 Northdale Oaks Dr., Tampa, Fla. 33624; Irwin Hanopole, 33 Colonial Woods Dr., West Orange, N.J. 07052

[21] Appl. No.: 5,519

[22] Filed: Jan. 20, 1987

[51] Int. Cl.⁴ .............................................. B65B 43/32
[52] U.S. Cl. ....................................... 141/114; 206/525; 220/345; 229/9; 53/390; 294/1.3; 383/36; 383/43
[58] Field of Search ............... 141/10, 67, 68, 114, 141/313–317, 390, 391, 392; 229/9; 220/345; 150/153; 294/1.3; 206/525; 383/36, 43, 87; 53/390

[56] References Cited

U.S. PATENT DOCUMENTS

| | | | |
|---|---|---|---|
| 112,727 | 3/1871 | Lum | 141/390 |
| 533,044 | 1/1895 | Bingham | 229/9 |
| 1,023,276 | 4/1912 | Rouse | 220/345 |
| 1,562,641 | 11/1925 | Hodgson | 150/153 |
| 2,428,267 | 9/1947 | Doppelt | 150/153 |
| 2,430,155 | 11/1947 | Buttery | 248/95 |
| 2,802,565 | 8/1957 | Kabbash | 229/9 |
| 3,251,390 | 5/1966 | Evans . | |
| 3,286,826 | 11/1966 | Stou | 294/1.3 |
| 3,779,496 | 12/1973 | Welles | 248/99 |
| 3,915,329 | 10/1975 | Zaks | 220/65 |
| 3,934,803 | 1/1976 | Paulus, Jr. | 248/99 |
| 3,936,087 | 2/1976 | Alexander | 294/1.3 |
| 3,978,540 | 9/1976 | Peck et al. | 294/1.3 |
| 3,983,914 | 10/1976 | Benson | 141/390 |
| 4,014,157 | 3/1977 | Pearce . | |
| 4,037,778 | 7/1977 | Boyle | 229/55 |
| 4,182,336 | 1/1980 | Black . | |
| 4,205,869 | 6/1980 | Mathis | 294/1.3 |
| 4,215,888 | 8/1980 | Gavin et al. | 94/1.3 |
| 4,585,124 | 4/1986 | Pride | 206/525 |
| 4,686,814 | 8/1987 | Yanase | 383/36 |

FOREIGN PATENT DOCUMENTS

375694 6/1932 United Kingdom ................... 229/9

Primary Examiner—Henry J. Recla
Assistant Examiner—Ernest Glusick
Attorney, Agent, or Firm—Nilsson, Robbins, Dalgarn, Berliner, Carson & Wurst

[57] ABSTRACT

A bag assembly which includes a sealable bag and an insert slidably positioned therein, which assembly inlcudes a mechanism for restraining the complete withdrawal of the insert from out of the bag. The insert is formed to be at least lengthwise arcuately flexed in a manner to substantially open the bag mouth and allow for the disposal of materials into the bag.

11 Claims, 4 Drawing Sheets

RECEPTACLE BAG ASSEMBLY

BACKGROUND OF THE INVENTION

The invention relates to packaging apparatus and techniques, and more specifically to a sealable bag assembly including an insert slidably positionable in the bag, which insert can be manipulated to both open the mouth of the bag and form a chute for directing tampons and the like into the bag.

The users of tampons and other types of sanitary products must, in some manner, dispose of these products after use. Typically, these products are either flushed down a toilet or disposed of in a suitable garbage receptacle; however, when such receptacles are not readily available to the individual these types of sanitary products must be wrapped and retained until a suitable receptacle can be found. Further, even when a suitable receptacle is available it is sometimes appropriate to wrap the product prior to disposal, particularly when using a receptacle in a public facility.

In order to make the disposal of these types of sanitary products, particularly tampons, much more convenient, those companies which produce and package these products include with the products suitable disposal bags. Further, many public and private toilet facilities provide suitable disposal bags for users of tampons and other sanitary products.

One particular disadvantage in using such bags for disposing of tampons or the like is the difficulty of opening the bag while placing the tampon therein.

There are, however, various types of devices which can be inserted into a bag to maintain the bag mouth open while also functioning as a chute for directing material into the now open bag. Example of such devices are disclosed in U.S. Pat. Nos. 112,727, issued to Lum; 4,037,778 issued to Boyle; 2,430,155 issued to Buttery; 3,915,329 issued to Zaks; 3,934,803 issued to Paulus; 3,779,497 issued to Welles; 3,936,087 issued to Alexander; 9,993,914 issued to Benson; and 4,014,157 issued to Pearce.

The type of devices disclosed by the above-referenced patents are generally cumbersome to use and are not constructed to be carried conveniently with products, such as tampons.

An example of a disposal bag constructed to be conveniently carried with a sanitary napkin is disclosed in U.S. Pat. No. 4,182,336 issued to Black. The bag is attached to the underside of the sanitary napkin, and can be opened and repositioned for receiving the napkin after use. However, the user must physically maintain the bag open while inserting the napkin.

Bags have also be constructed in such a manner as to allow them to be easily opened, such as the bag disclosed in U.S. Pat. No. 3,251,390 issued to Evans. The disclosed bag is formed with a flexible plate secured contiguous its mouth. The plate when gripped and flexed causes the bag mouth to open.

It is thus apparent that the need exists for a convenient and economically constructed bag assembly which is designed to allow a user to easily retain open the bag mouth, and include a mechanism which will direct the material into the bag.

SUMMARY OF THE INVENTION

The present invention accomplishes the above objectives by providing a bag assembly including an insert which is slidably fitted in and out of the bag. This insert can be selectively manipulated to expand open the bag mouth and act as a ramp for directing materials, particularly a tampon, inside the bag.

In order to open the bag mouth the insert is partially withdrawn from the bag and flexed along its length in a manner which will be described further herein. As a result of flexing the insert the bag mouth is opened and the insert is conformed to function as a curved chute for directing material into the bag.

In order to properly position the insert prior to it being flexed the bag assembly includes a catch mechanism which restrains the complete withdrawal of the insert from out of the bag.

The bag assembly can be further modified to include an arcuately flexible member which is secured transversely across the insert, such that when the insert is flexed this member will also flex, but in an opposite manner. Thus, when both the insert and this member are flexed they will in combination fully extend open the bag mouth.

The bag assembly is also provided with a means for effecting the closure of the bag mouth to prevent the loss of any material deposited in the bag.

BRIEF DESCRIPTION OF THE DRAWINGS

The present invention may be better understood and its numerous objects and advantages will become apparent to one skilled in the art from the accompanying drawings, wherein like-referenced numerals refer to like elements of the figures, and wherein.

DESCRIPTION OF THE PREFERRED EMBODIMENT

The invention is directed to a bag assembly including an insert which is formed to be slid into and out of the bag. The bag and insert are formed to cooperate in such a manner to restrain the complete withdrawal of the insert from out of the bag. This will position the insert such that when it is manipulated for lengthwise flexure the mouth of the bag will sufficiently expanded open to allow insertion of any material into the bag.

The bag assembly of the invention is advantageously used for the disposal of tampons, or other types of similarly sized sanitary products. However, the bag assembly may also be utilized for the disposal of any other type of material. Thus, for example, the bag assembly of the invention may be utilized for disposal of food scraps, with the insert functioning as a shovel or chute for directing the scraps into the bag.

Figures 1A, 1B:
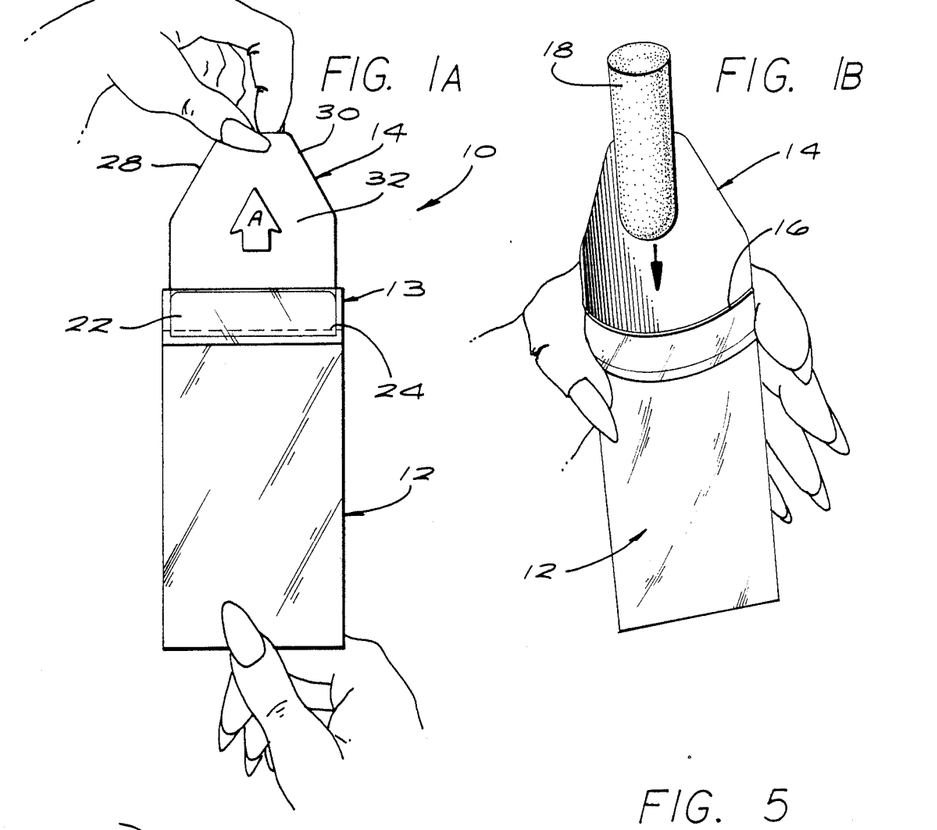
FIGS. 1A–1C illustrate the operation of the receptacle bag assembly in accordance with one embodiment of the invention.
Figure 1C:
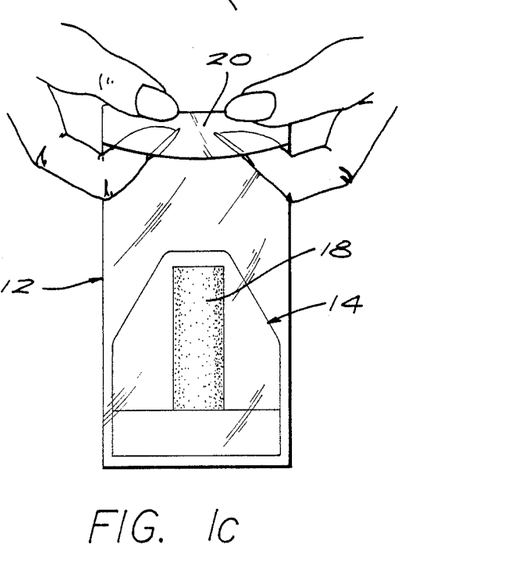

Referring now more specifically to FIGS. 1A-1C, a bag assembly in accordance with an embodiment of the invention is seen generally at 10. The bag assembly 10 of the invention includes a bag 12, with an insert 14 positioned therein. The bag 12 is typically formed by adhering together two sheets of a flexible material, for example plastic, along their respective side and bottom edges. The bag 12 will thus have an open top end or a mouth 16 as defined by the nonattached top edges of the two sheets of flexible material.

The bag mouth 16 can be opened by an individual for insertion of material therein. As seen in the FIGS. 1A-1C, the insert 14 is formed to be slide into and out of the bag 12.

Generally, the insert 14 is a normally flatwise disposed board which is sized to fit easily into the bag 12. The insert 14 may be constructed from any suitable material, such as paper, cardboard or plastic. The actual thickness of the insert 14 is not critical to the invention, provided that the insert 14 is formed for flexure at least along its length.

As seen in FIG. 1A, the insert 14 is being pulled by an individual out of the bag 12, with one of the individual's hands gripping the insert 14 and the other hand gripping the bag 12, in a direction indicated by arrow A. The insert 14 is restrained from being completely withdrawn from out the bag 12 by a suitably provided catch mechanism, which will be described more fully herein, indicated generally at 13.

Once the insert 14 has been pulled out of the bag 12 as far as the catch mechanism 13 will allow the individual can, by inwardly pressing the longitudinal sides of the insert 14 cause the insert 14 to arcuately flex in a lengthwise manner, as seen in FIG. 1B. This arcuate flexing of the insert 14 will cause the bag mouth 16 to be forced open, especially when the insert 14 is being flexed along its length contiguous the bag mouth 16. A tampon 18 may be placed in the bag 12 through the now open bag mouth 16. Furthermore, the arcuately shaped insert 14 can function as a chute by sliding the tampon 18 into the bag along the surface of the insert 14.

With the tampon 18 now situated inside the bag, the individual can reinsert the insert 14 into the bag and seal the bag mouth 16 by any appropriate means.

As illustrated in FIG. 1C, one of the sheets forming the bag 12 is formed with an outer cuff 20 contiguous to the bag mouth 16. This cuff 20 is formed by constructing the bag 12 from two sheets of different lengths, such that the longer sheet will extend past the other along the bag mouth 16. This extended portion of the sheet is folded over and sealed to the bag 12 along its side edges leaving its lower end free of the bag 12.

By inverting this cuff 20 and folding it back over the bag 12 the bag mouth 16 can be closed, as shown in FIG. 1C.

An example of a cuff construction for use with the bag assembly 10 of the invention is disclosed in U.S. Pat. No. 2,709,467, issued to Hoeppner on May 31, 1955, which disclosure is incorporated herein by reference.

Thus, the bag assembly 10 of the invention allows an individual to conveniently expand open the bag mouth 16 by arcuately flexing the insert 14 and place a tampon therein using the insert 14 as a chute.

As previously stated, the bag assembly 10 is formed with a catch mechanism 13 which functions to restrain the complete withdrawal of the insert 14 from out of the bag 12. In accordance with a particularly preferred embodiment of the invention, this catch mechanism 13 includes a catch flap 22, which interacts with and can become lodged in a cuff 24 when brought into engagement therewith.

The catch flap 22 is secured to the insert 14 in a manner, as will be further described herein, so that it will angle upwardly, out from the insert 14. The cuff 24 is formed inside the bag 12, along the bag mouth 16 in a similar manner as described above for the cuff 20 with only its sides being secured to the bag 12. This directs the opening of the cuff 24 downward so that when the insert 14 is being pulled out of the bag 12 the catch flap 22 will be properly positioned to enter and become lodged into the interior cuff 24. This restrains any further withdrawal of the insert 14 from out of the bag 12.

Figure 4:
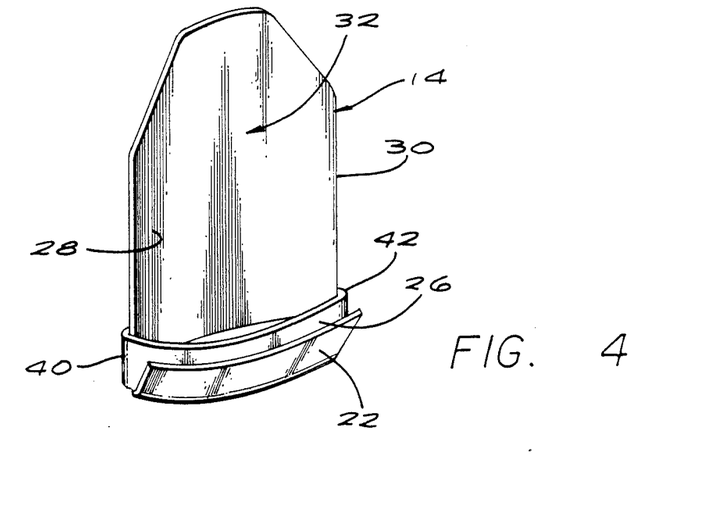

To further facilitate the opening of the bag mouth 16, the insert 14 is preferably formed with a cross-wise lying collar 26, as seen better in FIG. 4. This collar 26 is secured only by its lateral most side ends to the insert 14, with its top and bottom sides remaining free. The collar 26 is formed from a material, which while being normally disposed in a flatwise relation to the insert 14, can be arcuately flexed or bowed outward by pressing inwardly on its side ends.

Thus, since the collar 26 is secured to the insert 14, by inwardly pressing the side edges of the insert 14 and the side ends of the collar 26 simultaneously, both will be arcuately flexed; however, by properly manipulating the collar 26 it can be arcuately flexed in a direction out away from the insert 14. The arcuate flexure of the insert 14 and the collar 26 will in combination define a ring-like structure which substantially expands open the bag mouth 16. This allows for the easier insertion of any material, such as a tampon 18, into the bag 12.

As illustrated in FIGS. 1A-1C, the catch flap 22 is integrally formed from the collar 26. In this manner, when the catch flap 22 becomes lodged in the interior cuff 24 the collar 26 will be positioned contiguous the bag mouth 16. This positions the collar 26 at its most advantageous position for opening the bag mouth 16 when it is properly manipulated.

By utilizing the insert 14 as a chute, the insertion of various materials into the bag 12 is made easier. In this regard, that end of the insert 14 which will extend out of the bag 12 is formed with its sides 28 and 30 inwardly angled, as shown in FIG. 1A. This allows that end of the insert 14 to act somewhat as a funnel and be more easily positioned in restricted areas.

Figure 5:
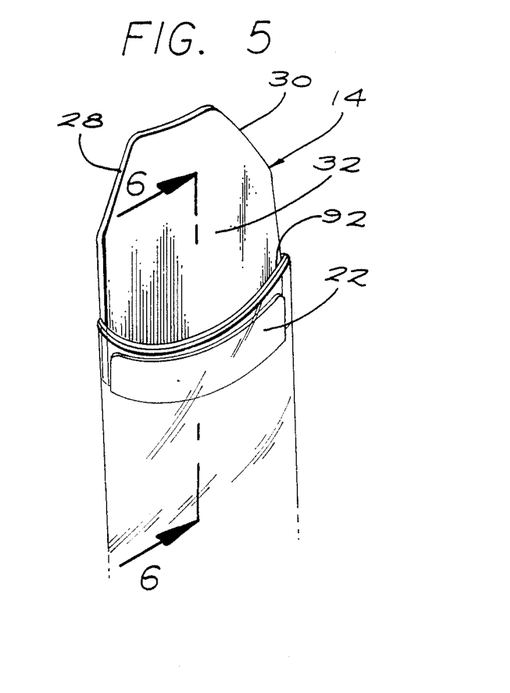
FIG. 5 is a front perspective view of an embodiment of the invention.
Figures 6, 7, 8, 9:
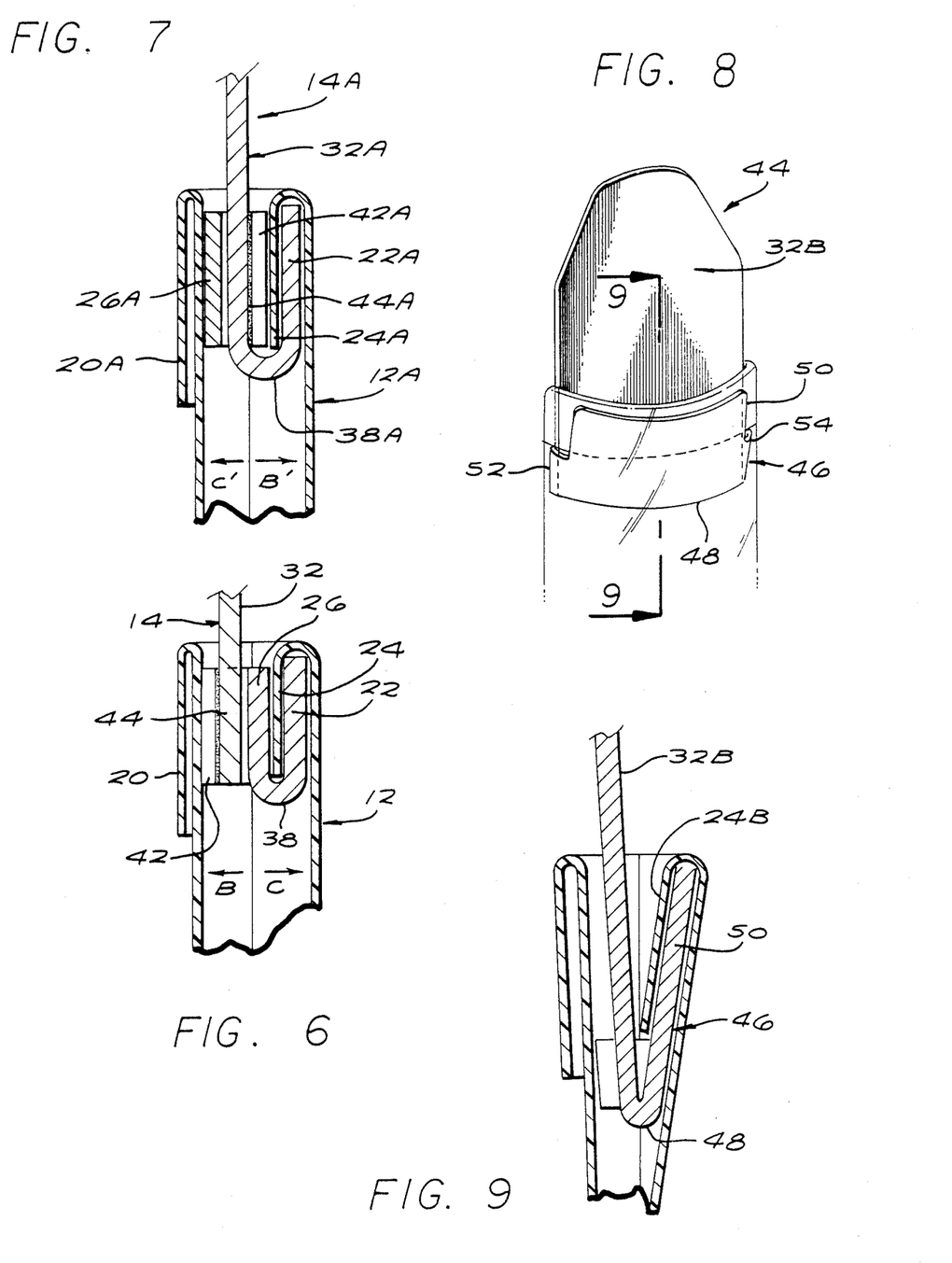
FIG. 6 is a cross-sectional view of FIG. 5 along line 6—6.
FIG. 7 is a cross-sectional view similar to that shown in FIG. 6 except with a differing insert embodiment.
FIG. 8 is a perspective view of another embodiment of the invention.
FIG. 9 is a cross-sectional view of the embodiment illustrated in FIG. 8 along line 9—9.

Referring specifically to FIGS. 4, 5 and 6, the insert 14, illustrated and discussed in relation to FIGS. 1A-1C, will now be described in greater detail.

The insert 14 includes a body portion 32 which is formed from a normally flat-lying board that is at least lengthwise flexible. This body portion 32 can thus be manipulated to be arcuately flexed along its length by inwardly pressing its side edges 34 and 36 toward each other. This, as discussed above, will cause the opening of the bag mouth 16 when the insert 14 is properly positioned in the bag 12.

The insert body portion 32 is dimensioned so that it may be easily slid into and out of the particular bag 12. The insert body portion 32 is also preferably formed with its two sides 28 and 30 angled inwardly as seen in FIGS. 4 and 5, along that portion of its length which can be positioned out of the bag 12. This inward angling of the body portion sides 28 and 30 allows the insert 14 to be more easily positioned in a confined area.

The insert 14, as discussed above, is further formed with the collar 26 and the catch flap 22. In the embodiment illustrated in FIGS. 4, 5 and 6, the catch flap 22 and collar 26 are one integral piece which is secured in a suitable manner to the insert body portion 32.

As discussed above, the catch flap 22 is formed so that it will normally angle upward away from the remaining portion of the insert 14. As better seen in FIG. 4, the combined structure of the collar 26 and catch flap 22 is positioned transversely across the insert body portion 32. The catch flap 22 is secured along its lowermost end 38 to the collar 26. The manner by which this catch flap 22 is secured to the collar 26 ensures that the catch flap 22 will normally angle outward away from the collar 26 and thus the remainder of the insert 14.

Typically, the catch flap 22 is formed from the same piece of material used to form the collar 26. A scoring (not shown) is then made between that portion of the material piece which will define the collar 26 and that portion which will define the catch flap 22. The piece of material is then folded along this scoring. This scoring is made at a depth and in a manner to ensure that the catch flap 22 will be normally disposed at an angle away from the collar 26. As a result of this construction, the catch flap 22 can be said to have a "memory" with regard to its angled position, that is, if the flap 22 is flattened against the collar 26, it will return to its angular position once released.

This angular positioning of the catch flap 22 is particularly critical to ensure that it will be directed into and become lodged in the interior cuff 24 when the insert 14 is being pulled out of the bag 12. This lodged relationship of the catch flap 22 in the internally disposed cuff 24 is better seen in FIG. 6.

The collar 26 is formed from a material which will allow it to be at least arcuately flexed by the inward pressing of its laterally placed ends, which ends 40 and 42 are secured in a suitable manner to the sides of the insert body portion 32. This allows the body portion 32 and the collar 26 to be manipulated to be arcuately flexed out away from each other in opposite directions, as indicated by the arrows B and C shown in FIG. 6. The result is that the arcuately flexed insert body portion 32 and collar 26 will, in combination, define a substantially circular structure, which when positioned contiguous the bag mouth 16 will substantially expand open the bag mouth 16, as best seen in FIG. 5.

As stated, the collar ends 40 and 42 are secured to the insert body portion 14 in a suitable manner. As illustrated in FIGS. 4 and 6, these ends 40 and 42 are bent about and secured to the insert body portion 32 by any suitable adhesive, with the end 42 shown adhered by an adhesive layer 44 to the insert body portion 32 in FIG. 6.

While the collar 26 and catch flap 22 combination are showed adhered adjacent to the lowermost end of the insert body portion 32, that is, the end of the insert body portion 32 which will be placed first into the bag 12, this catch flap 22 and collar 26 combination can be positioned at any location along the length of the insert body portion 32. However, in order to ensure that a substantial portion of the insert body portion 32 can be pulled out from the bag 12, the catch flap 22 and collar 26 combination are preferably positioned nearer the lowermost end of the insert body portion 32 as best seen in FIGS. 4, 5 and 6.

It should further be noted that while the embodiment of the assembly 10 which has been described includes an internally defined cuff 24, as illustrated in FIG. 5 this cuff 24 may be replaced by a transversely secured material strip 92 that is secured only by its ends to the bag 12. This material strip 92 will function in a manner similar to the manner described for the cuff 24, in that the catch flap 22 will become lodged against this strip 92 when the insert 14 is being pulled out of the bag 12.

While both the catch flap 22 and collar 26 have been described and illustrated as a single, integrally formed construction, this is not a necessary aspect of the invention.

Referring now to the remaining figures various other embodiments of both the insert 14 and the bag 12 will be described in greater detail.

Figures 2, 3:
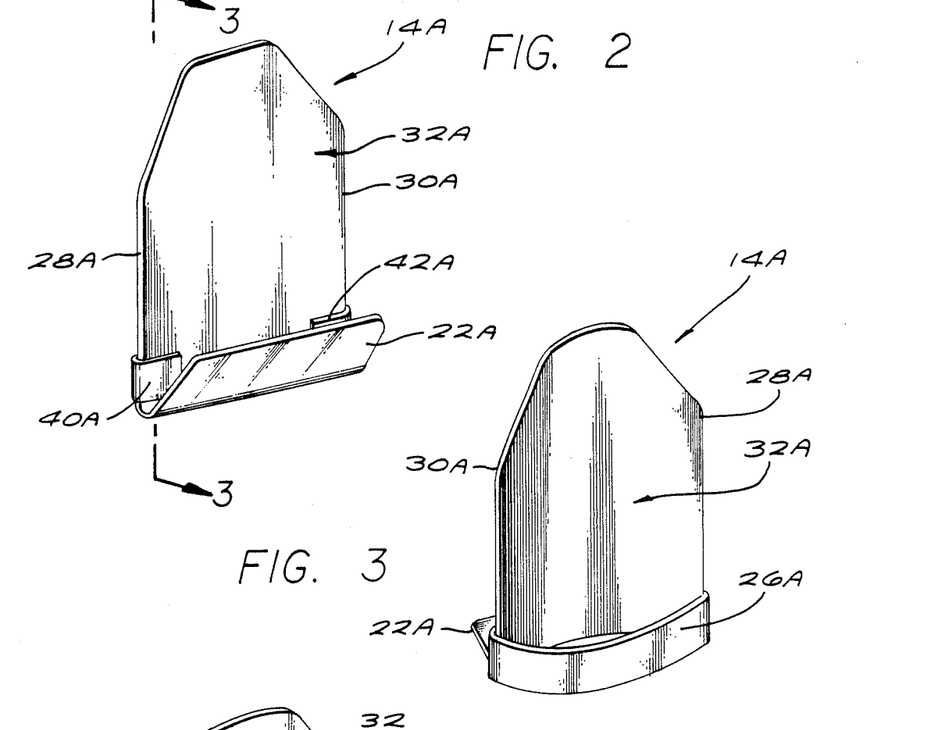
FIGS. 2–4 are perspective views of various inserts in accordance with embodiments of the invention.

Specifically referring to FIGS. 2, 3 and 7, another embodiment of the invention will now be described in greater detail.

In this embodiment, the bag 12A is constructed in a manner similar to the construction of the bag 12 illustrated in the FIGS. 4, 5 and 6. However, the insert 14A differs from the insert 12 described above in that the collar 26A and catch flap 22A are secured to opposite sides of the insert body portion 32A.

In this regard, the catch flap 22A is formed in a similar manner as the catch flap 22 described above to ensure that it will angle upward and outward from the insert 12A. This catch flap 22 is formed by forming a transversely oriented scoring (not shown) along a lower portion of the insert body portion 32A with the body portion 32A being folding along this scoring to define the catch flap 22A, as seen in FIG. 2. The catch flap 22 is thus secured along the lowermost end 38A of the insert body portion 32A, as best seen in FIG. 7.

The collar 26A is formed from an elongated strip of material which is positioned tranversely across the insert body portion 32A and secured thereto in a manner similarly described above for the securing of the collar 26 to the insert body portion 32, that is the respective ends 40A and 42A of the collar 26A are bent about and adhered by an adhesive layer 44A to the insert body portion 32A.

Again, by inwardly pressing the respective sides 28A and 30A of the insert body portion 32A in conjunction with the respective ends 40A and 42A of the collar 26A, both the insert body portion 32A and the collar 26A are manipulated to be arcuately flexed to define in combination a circular structure that substantially opens the bag mouth 16, particularly when the collar 26A is positioned contiguous thereto. The direction at which the collar 26A and insert body portion 32A will be arcuately flexed is shown in FIG. 7 by arrows C' and B'.

Also, as seen in FIG. 7, the angular relationship of the catch flap 22A ensures that it will be lodged in the interior cuff 24A, thus restraining the complete withdrawal of the insert body portion 32A from out of the bag 12A.

Referring now to FIGS. 8 and 9, another assembly insert embodiment will be described in greater detail. This particular insert may be used in combination with the already described bags 12 and 12A. In accordance with this embodiment, an insert 44 which, while being substantially similar in some respects to inserts 14 and 14A of the previously discussed embodiments, is in some respects different. Specifically, this particular insert 44 includes a body portion, as indicated at 32B, that is substantially the same as the body portions 32 and 32A discussed above. However, the collar and the catch flap of this embodiment differ somewhat from the collars and catch flaps discussed above. Furthermore, when the insert and collar of this embodiment are simultaneously flexed there is no separation between their lowermost ends.

As seen in FIG. 8, a single combined collar and catch flap structure is shown generally at 46. This combined collar and catch flap assembly 46 is formed in a manner similar to the manner by which the catch flap 22A is formed in the embodiment of FIGS. 2, 3 and 7. That is, the lowermost end of the insert body portion 32B is scored and folded crosswise upon itself. This forms a lower end 48 joining the collar and catch flap assembly 46 to the insert body portion 32B. However, the assembly 46 which is formed in this manner will normally be disposed in a flatwise relation to the insert body portion 32B. This includes that portion of the assembly 46 which is to function in a similar manner to the catch flaps 22 and 22A, which as described above normally angle outward and upward away from the insert body portion.

That portion of the assembly 46 which is to function as the above discussed catch flaps is indicated generally as, a flap portion 50. This flap portion 50 is similar in shape to the previously discussed catch flaps 22 and 22A and is situated as the uppermost portion of the assembly 46. The assembly 46 is secured to the insert body portion 32 by adhering its lateral most ends 52 and 54 to the insert body portion 32. As illustrated, these respective ends 52 and 54 do not extend along the entire side of the assembly 46 so not as to be formed out from the catch portion 50. This will allow the catch portion 50 to be free from the insert body portion 32B at its laterally-most disposed ends which is necessary in order to allow the flap portion 50 to become lodged into the internally disposed cuff 24B, as seen in FIG. 9.

Unlike the embodiments previously discussed, the embodiment illustrated in FIGS. 8 and 9 will not, when the respective sides of the insert body portion 32B and the assembly 46 are inwardly pressed form the ring-shaped structure through which material may be passed through. In accordance with this embodiment, when the respective sides of the insert body portion 32B and assembly 46 are inwardly pressed a V-shaped cup is formed. This V-shaped cup will sufficiently open the bag mouth 16B to allow for the depositing of any material into the bag 12. The material to be deposited will in fact slide into the V-shaped cup, as defined by the assembly 46 and the insert 44 and will not become deposited inside the respective bag 12B until the insert 44 has been slid back down into the bag 12B.

Figure 10:
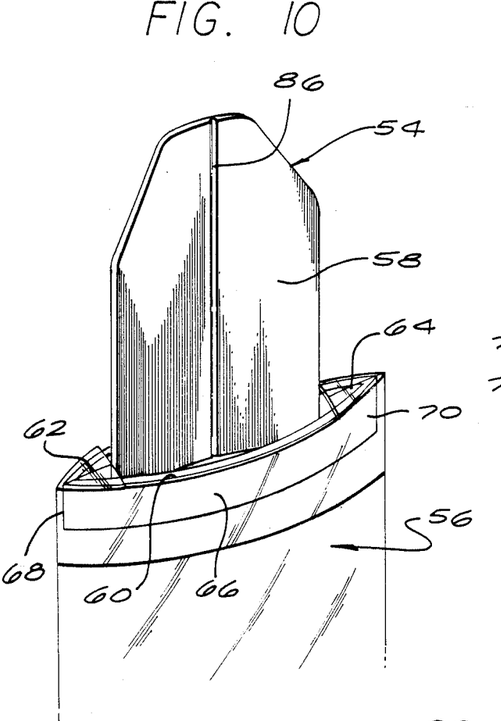
FIG. 10 is a partially sectioned perspective view of still another embodiment of the invention.

Referring now more specifically to FIG. 10, another embodiment of the invention will be discussed. An insert 54 is shown positioned within a bag 56. This insert 54 is formed with a body portion 58 similar in shape and construction to those inserts described for the previously discussed embodiments. However, the insert 54 does not include a catch flap for use in restraining withdrawal of the insert 54 out of the bag 56, nor does the bag 56 include an internally disposed cuff into which a catch flap would become lodged. Instead, the insert body portion 58 is formed with two opposite laterally projecting shoulders 68 and 70 which will engage and restrain further movement of the insert 54 out of a bag 56 that is appropriately formed to include a mouth 60 which is narrower in width than the width of the shoulders 68 and 70. This mouth 60 is formed by sealing the bag 56 upper end at least partially inward from its sides to define two opposite corners 62 and 64. These two corners 62 and 64 will be engaged by the laterally projecting shoulders 68 and 70 of the insert 54 and thus restrain any further withdrawal of the insert 54 out from the bag 56.

In accordance with the embodiment illustrated in FIG. 10, these laterally projecting shoulders 68 and 70 of the insert 54 are defined by a collar 66, which is adhered to the insert body portion 58 in a manner similar to that discussed above but is formed to extend laterally outward from the respective sides of the insert body portion 58. Thus, as the insert 54 is being drawn out from the bag 56 these ends of the collar 66 which define the shoulders 68 and 70 will engage the corners 62 and 64 and restrain any further withdrawal of the insert 54 out from the bag 56.

In constructing the embodiment illustrated in FIG. 10, the insert 54 will be from a material which is longitudinally flexible enough so that it can be folded and inserted into the bag 56 through the more narrow mouth 60, despite the fact of the wider shoulders 68 and 70.

Figure 11:
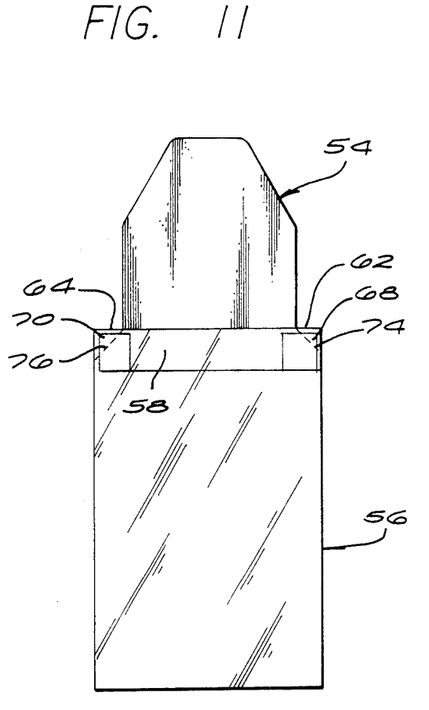
FIG. 11 is a front view of still another embodiment of the invention.

To allow for more of the insert 54 to be withdrawn from the bag 56 the respective shoulders 68 and 70 and the corners 62 and 64 can be diagonally formed, such as by cutting the respective corners and shoulders along the phantom lines 74 and 76 in FIG. 11. This would allow the insert 54 to be drawn further out from the bag 56.

Figure 12:
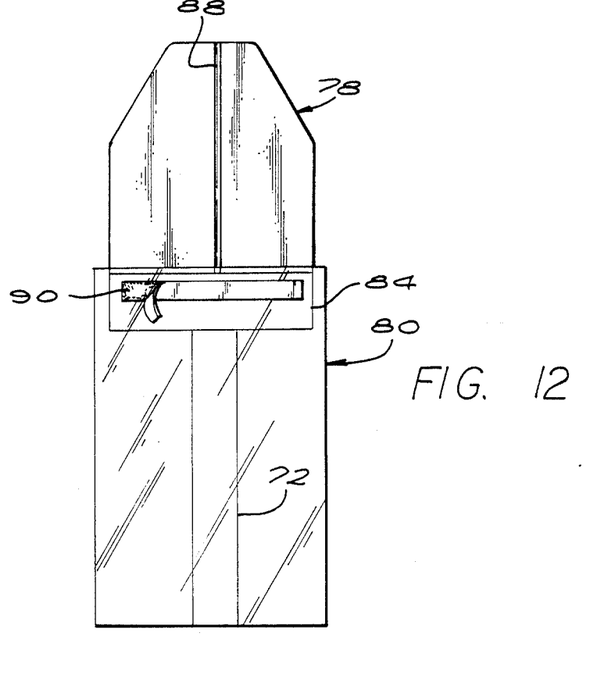
FIG. 12 is a front view of still a further embodiment of the invention.

A further method of restraining the withdrawal of an insert from out of a bag is illustrated by the embodiment of FIG. 12. In accordance with this embodiment, an insert 78 is secured to the bag 80 via a tail 72. This tail 72 is constructed from a flexible material to allow the tail 72 to be folded into the bag 80 when the insert 78 is inserted therein. For example, the tail 82 can be formed from paper or a plastic material. The tail 82 is secured at one end to the insert 78 and at its other end to the bottom of the bag 80. The length of the tail 82 should be sufficient enough to allow the insert 78 to be almost completely withdrawn from out of the bag 80. The insert 78 will also be formed with a collar 84, which collar 84 is similar in construction and function to the collar 26A discussed above for the embodiment illustrated in FIGS. 2, 3 and 7.

As already discussed, the inserts of the invention should be formed from a material which will allow for at least lengthwise flexure. This flexing along the length of the respective inserts can be further facilitated by providing a longitudinally disposed scoring, as indicated at 86 in FIG. 10 and at 88 in FIG. 12. This scoring will allow even a material of limited flexibility to be flexed in the manner described above to facilitate the opening of a bag.

It should also be noted that while the invention has heretofore only been illustrated and described with an externally disposed cuff for use in sealing the bag mouth any suitable bag construction or other modification to the assembly of the invention which will allow for sealing of the bag mouth may be utilized. For example, with reference to FIG. 12, a self-adhesive tape 90 may be adhered to one of the panels from which the bag 80 is constructed at a location contiguous to the bag mouth. Once material and the insert 78 have been positioned in the bag 80 this panel may be folded over and adhered to the other panel of the bag 80 using this tape 90.

Other methods for sealing a bag mouth would be apparent to those familiar with this art.

While the preferred embodiments have been described and illustrated herein, various modifications and substitutions may be made thereto without departing from the scope and spirit of the invention. Accordingly, it is to be understood that the present invention has been described by way of illustration and not limitation.

What is claimed is:

1. A bag assembly comprising:
   a bag having a first open end, wherein said bag is formed with a band secured laterally across the inside of said bag, with at least the lowermost end of said band being unattached to said bag;
   a chute insert which is formed to lie substantially flat for allowing said chute insert to be at least partially slid into and out from said bag through said open end, said chute insert being at least lengthwise elastically deformable to allow for its selective manipulation to be arcuately flexed, said chute insert being formed with a flap secured substantially across said insert, said flap being formed to normally angle upwardly and outwardly away from said insert, whereby said flap will engage said band when said chute insert is being withdrawn from said bag to restrain further movement of said insert out from said bag;
   collar means positioned along said bag open end with said collar means formed to lie in a substantially flat relationship with said chute insert, said collar means being selectively operable to be arcuately flexed away from said chute insert when said chute insert is manipulated to be arcuately flexed, whereby said chute insert and said collar means, when selectively operated to be arcuately flexed, push said two bag walls away from each other to open said bag open end; and
   closure means associated with said bag for at least temporarily closing said bag's open end.

2. The bag assembly of claim 1 wherein said flap is secured proximately to a first end of said chute insert, which chute insert's first end is placed first into said bag.

3. The bag assembly of claim 2 wherein said band is a strip of material secured crosswise inside said bag proximate said open end.

4. The bag assembly of claim 2 wherein said band is an internal cuff formed contiguous to said bag's first open end, said cuff defined by at least a first wall secured in said bag to provide an opening facing in a direction opposite said bag opening.

5. The bag assembly of claims 3 or 4, wherein said collar means is secured to said chute insert and is formed to be manipulated for arcuate flexure outward away from said chute insert when said chute insert is flexed.

6. A bag assembly comprising:
   a bag defined by two opposing walls interconnected along their side lengths and along their bottom length, with said top lengths being at least partially unconnected to define an opening into said bag, said bag walls lying in a normally flat relation, wherein said bag is formed with a band secured laterally across the inside of said bag, with at least the lowermost end of said band being unattached to said bag;
   a chute insert which is formed to lie substantially flat for allowing said chute insert to be at least partially slid into and out from said bag through said open end, said chute insert being at least lengthwise elastically deformable to allow for its selective manipulation to be arcuately flexed, said chute insert being formed with a flap secured laterally across the lowermost end of said insert, said flap being formed to normally angle upwardly and outwardly away from said insert, whereby said flap will engage said band when said chute insert is being withdrawn from said bag to restrain further movement of said insert out from said bag;
   collar means connected to said chute insert with said collar means formed to be normally disposed in a substantially flat position in relation to said insert, said collar means being selectively operable to be arcuately flexed away from said chute insert when said chute insert is manipulated to be arcuately flexed, whereby said chute insert and said collar means, being selectively operable to be arcuately flexed, push said two bag walls away from each other to open said bag open end; and
   closure means associated with said bag for at least temporarily closing said bag's first open end.

7. The bag assembly of claim 6 wherein said collar means comprises a substantially flat elongated member secured lengthwise across said chute insert, said member being formed to bow outward away from said panel when said panel is manipulated to be arcuately flexed.

8. The bag assembly of claim 7 wherein said band is an internal cuff formed contiguous to said bag's first open end, said cuff defined by at least a first wall secured in said bag to provide an opening facing in a direction opposite said bag opening.

9. The bag assembly of claim 7 wherein said band is a strip of material secured by its lateral most ends inside and crosswise said bag.

10. A tampon disposal pouch comprising:
    a bag defined by two opposing walls interconnected along their side lengths and along their bottom length, with said top lengths being at least partially unconnected to define an opening into said bag, said bag walls lying in a normally flat relation;
    a chute insert which is formed to lie substantially flat for allowing said chute insert to be at least partially slid into and out from said bag through said open end, said chute insert being at least lengthwise elastically deformable to allow for its selective manipulation to be arcuately flexed;
    a substantially planar flap secured at least along its lower end to said chute insert in a crosswise fashion, said flap being formed to normally angle upwards and outwardly away from said chute insert;
    a portion of said bag which is formed as an internal cuff contiguous to said bag's first open end, said cuff defined by at least a first wall secured in said bag to provide an opening facing in a direction opposite said bag opening;
    a substantially flat elongated member secured lengthwise across said chute insert, said member being normally disposed to lie in a flat relationship with said chute insert and selectively operable to be arcuately flex away from said chute insert when said chute insert is manipulated to be arcuately flexed, whereby said chute insert and said elongated member when selectively operated to be arcuately flexed, push said two bag walls away from each other; and an outer cuff formed continguous to said bag opening which is manipulatable for at least temporarily closing said bag's first open end.

11. A bag assembly comprising:

a bag defined by two opposing walls interconnected along their side lengths and along their bottom length, with said top lengths being at least partially unconnected to define an opening into said bag, said bag walls lying in a normally flat relation;

a chute insert which is formed to lie substantially flat for allowing said chute insert to be at least partially slid into and out from said bag through said open end, said chute insert being at least lengthwise elastically deformable to allow for its selective manipulation to be arcuately flexed, said chute insert being formed with two opposite lateral projecting shoulders contiguous to a first end thereof, which first end is placed first into said bag, with said bag opening being formed to only allow passage therethrough of said chute insert but not said lateral projecting shoulders;

collar means connected to said chute insert, which is formed to lie in a substantially flat relationship with said chute insert, said collar means being selectively operable to be arcuately flex away from said chute insert when said chute insert is manipulated to be arcuately flexed, whereby said chute insert and said collar means, when selectively operated to be arcuately flexed, push said two bag walls away from each other to open said bag open end; and closure means associated with said bag for at least temporarily closing said bag's first open end.

* * * * *